US007947856B2

(12) United States Patent
Mathieu et al.

(10) Patent No.: US 7,947,856 B2
(45) Date of Patent: May 24, 2011

(54) PROCESS FOR THE PREPARATION OF HALOGENATED HYDROCARBONS WITH AT LEAST 3 CARBON ATOMS IN THE PRESENCE OF IRON AND A PHOSPHITE

(75) Inventors: Veronique Mathieu, Wavre (BE); Francine Janssens, Vilvoorde (BE)

(73) Assignee: SOLVAY (Societe Anonyme), Brussels (BG)

( * ) Notice: Subject to any disclaimer, the term of this patent is extended or adjusted under 35 U.S.C. 154(b) by 63 days.

(21) Appl. No.: 12/442,900

(22) PCT Filed: Oct. 5, 2007

(86) PCT No.: PCT/EP2007/060599
§ 371 (c)(1),
(2), (4) Date: Mar. 25, 2009

(87) PCT Pub. No.: WO2008/040803
PCT Pub. Date: Apr. 10, 2008

(65) Prior Publication Data
US 2009/0247794 A1    Oct. 1, 2009

(30) Foreign Application Priority Data

Oct. 6, 2006    (EP) .................................... 06121916

(51) Int. Cl.
*C07C 17/26* (2006.01)
*C07C 17/00* (2006.01)

(52) U.S. Cl. ........................................ 570/257; 570/165
(58) Field of Classification Search ................. 570/257, 570/165
See application file for complete search history.

(56) References Cited

U.S. PATENT DOCUMENTS

| 4,605,802 A | 8/1986 | Astrologes |
| 5,917,098 A | 6/1999 | Bertocchio et al. |
| 6,399,839 B1 | 6/2002 | Mathieu et al. |
| 6,399,840 B1 | 6/2002 | Schoebrechts et al. |
| 6,441,256 B1 | 8/2002 | Mathieu et al. |
| 6,500,993 B1 | 12/2002 | Mathieu et al. |

FOREIGN PATENT DOCUMENTS

| EP | 787707 A1 | 8/1997 |
| EP | 999196 A1 | 5/2000 |
| WO | WO97/07083 A1 | 2/1997 |
| WO | WO98/50329 A1 | 11/1998 |
| WO | WO98/50330 A1 | 11/1998 |
| WO | WO00/35839 A1 | 6/2000 |

OTHER PUBLICATIONS

JP abstract 2001213820, Aug. 7, 2001.*

* cited by examiner

*Primary Examiner* — Jafar Parsa
(74) *Attorney, Agent, or Firm* — Beatrice C. Ortego

(57) ABSTRACT

A telomerisation process is described whereby haloalkanes like tetrachloromethane are added to halogenated olefins like 2-chloroprop-1-ene in the presence of an iron catalyst and a phosphite. The reaction products, e.g. 1,1,1,3,3-pentachlorobutane, can be fluorinated.

10 Claims, No Drawings

PROCESS FOR THE PREPARATION OF HALOGENATED HYDROCARBONS WITH AT LEAST 3 CARBON ATOMS IN THE PRESENCE OF IRON AND A PHOSPHITE

CROSS-REFERENCE TO RELATED APPLICATIONS

This application is a U.S. national stage application under 35 U.S.C. §371 of International Application No. PCT/EP2007/060599 filed Oct. 5, 2007, which claims priority to European Application No. 06121916.8 filed Oct. 6, 2006, these applications being herein incorporated by reference in their entirety for all purposes.

The instant invention concerns a process for the preparation of halogenated hydrocarbons comprising at least 3 carbon atoms by catalytic reaction between a haloalkane and an olefin.

Halogenated hydrocarbons can be prepared by the addition of haloalkanes to olefins.

EP-A-0 787707 (U.S. Pat. No. 5,917,098) discloses the preparation of 1,1,1,3,3-pentachlorobutane from tetrachloromethane and 2-chloro-prop-1-ene in the presence of a copper halide and certain amines.

WO 98/50330 (U.S. Pat. No. 6,399,839) discloses the preparation of chloroalkanes or chlorofluoroalkanes by the addition of haloalkanes, such as tetrachloromethane, 1,1,1-trichloroethane or 1,1,1-trichloro-2,2,2-trifluoroethane to olefins which may contain halogen atoms. In that process, an organically substituted copper compound is used as catalyst; a polar solvent and/or a cocatalyst selected among amines, amides and trialkyl phosphinoxides. Especially preferred compounds to be prepared are 1,1,1,3,3-pentachlorobutane and 1,1,1,3-pentachloropropane.

WO 98/50329 (U.S. Pat. No. 6,399,840) discloses the preparation of 1,1,1,3,3-pentachlorobutane from tetrachloromethane and 2-chloroprop-1-ene in the presence of a copper (I) or copper (II) catalyst.

WO 97/07083 (U.S. Pat. No. 5,902,914) discloses a process for the preparation of halogenated hydrocarbons by the addition of haloalkanes to olefins in the presence of copper chloride and t-butylamine as cocatalyst.

Object of the present invention is to provide a process for the preparation of halogenated hydrocarbons applying novel catalysts.

This object and other objects are achieved by the process of the present invention.

The present invention concerns a process for the preparation of halogenated hydrocarbons with at least 3 carbon atoms by the reaction of a haloalkane and an olefin which is substituted by at least one halogen atom, in the presence of iron (Fe) and a phosphite. The term "phosphite" preferably denotes a compound of the formula $PR^1R^2R^3$. $R^1$, $R^2$ and $R^3$ are the same or different and are alkoxy groups of the formula $R^4O$ wherein $R^4$ is a saturated linear, branched or cyclic C1 to C10 alkyl group, or phenoxy groups of the formula $R^5O$ wherein $R^5$ denotes preferably phenyl. $R^4$ preferably denotes C1 to C5 alkyl. $R^1$, $R^2$ and $R^3$ are preferably the same. The reaction is especially preferably performed in the presence of triethylphosphite, tri-n-propylphosphite and tri-n-butylphosphite. Of course, if desired, mixtures of different phosphites may be applied.

The "molar" ratio (of course, iron is added in elemental form and thus, is calculated in the form of its atomic weight) between iron and the phosphite or, if different phosphites are used, the sum of phosphites, is generally equal to or lower than 50:1. Preferably, it is equal to or lower than 30:1. Generally, it is equal to or greater than 0.2:1. Preferably, it is equal to or greater than 5:1. if applied in the inventive process, the amount of phosphite is preferably selected such that the molar ratio between phosphite and olefin is greater than or equal to 0.01:1, especially preferably equal to or greater than 0.05:1. Preferably, that molar ratio is lower than or equal to 0.5:1.

The haloalkanes which are used in the process of the present invention generally are saturated organic compounds. Preferably, they have one to three carbon atoms. Preferably, they are substituted by at least two chlorine atoms. They may be substituted by other halogen atoms or by alkyl or halogenoalkyl groups. Preferably, the term "haloalkane" denotes alkanes which are substituted by one or more chlorine atoms or by one or more chlorine atoms and one or more fluorine atoms, but which do not include iodine atoms. Examples of very suitable haloalkanes are dichloromethane, trichloromethane, tetrachloromethane, 1,1,1-trichloroethane and chlorofluoroethanes like 1,1,1-trichloro-3,3,3-trifluoroethane, 1,1-dichloro-1-fluoroethane (HCFC-141b) and 1-chloro-1,1-difluoroethane (HCFC-142b). Tetrachloromethane is especially preferred.

The olefin which is used as starting material in the process of the present invention is generally ethylene, propylene or a butene, each of which is substituted by at least one halogen atom and optionally by alkyl groups, halogenoalkyl groups, nitril (CN) groups or carboxylic acid groups (COOH). Halogenated olefins are preferred. Chlorinated olefins are very suitable. Generally, they correspond to the formula $R^1R^2C=CClR^3$. In this formula, $R^1$, $R^2$ and $R^3$ independently represent H or Cl, linear, branched or cyclic alkyl or alkenyl, an aryl or a heteroaryl group. These alkyl, alkenyl, aryl or heteroaryl groups may be substituted. Examples for such halogenated olefins are vinyl chloride, vinylidene chloride, trichloroethylene, the isomers of chloropropene like 1-chloroprop-1-ene, 2-chloroprop-1-ene, and 3-chloroprop-1-ene. 2-chloroprop-1-ene is especially preferred.

Preferably, the addition of $CF_3CF_2I$ to vinyl fluoride in the presence of iron and triethyl phosphite is disclaimed.

If chlorofluoroalkanes like HCFC-141b or HCFC-142b are used as haloalkanes, chlorofluoroalkanes are obtained as reaction product.

The halogenated hydrocarbons obtained by the process of the present invention preferably belong to the family of chloropropanes, chlorobutanes and chloropentanes. The carbon atoms of the chloropropanes, chlorobutanes and chloropentanes can be substituted by other functional groups like other halogen atoms (e.g. bromine or iodine), alkyl groups, halogenoalkyl groups, nitrile (CN) groups or carboxylic acid groups (COOH). Chloropropanes, chlorobutanes and chloropentanes not substituted by such other functional groups are preferred.

Halogenated hydrocarbons of the general formula $C_nH_{(2n+2)-p}Cl_p$ are especially preferred reaction products. In this formula, n is an integer and stands for 3 or 4, p is an integer and stands for 3, 4, 5, 6 or 7. Examples of compounds which can be produced by the process of the present invention are 1,1,1,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1-dichloro-2-trichloromethylpropane. 1,1,1,3,3-pentachlorobutane and 1,1,1,3,3-pentachloropropane are preferred.

In a discontinuous process, the molar ratio between iron and olefin often is greater than or equal to 0.0005. Advantageously, it is equal to or greater than 0.001. Preferably, it is equal to or greater than 0.002. Often, the molar ratio between catalyst and olefin is lower than or equal to 1. Advantageously, it is lower than or equal to 0.5. Preferably, it is lower than or equal to 0.1.

In a continuous process, the molar ratio between iron or phosphite and the olefin should lie in the range given above for a discontinuous process, but it may reach higher upper limits, e.g. it could be up to 10; here, the upper limit is preferably lower than or equal to 1.

The amount of iron is expressed in a discontinuous process relative to the initial concentration of the olefin. In a continuous process, it is relative to the stationary concentration of the olefin in the reactor.

If desired, a solvent can be present during the reaction. Preferred solvents are aprotic. The haloalkane e.g. tetrachloromethane, may be used in excess and function as a reactant and as a solvent. If desired, the reaction products may be used as a solvent. Toluol is another suitable solvent, as well as hydrofluorocarbons like 1,1,1,3,3-pentafluorobutane.

The molar ratio between haloalkane, e.g. tetrachloromethane, and the olefin, e.g. 2-chloroprop-1-ene, can vary in a broad range. In general, the ratio is equal to or greater than 0.1. Advantageously, it is equal to or greater than 0.5. Preferably, it is equal to or greater than 1. Generally, the ratio is equal to or lower than 20. Advantageously, it is equal to or lower than 10. Preferably, it equal to or lower than 8. In case of such high ratios, the haloalkane also serves as a solvent.

Generally, the reaction is performed above ambient temperature. Preferably, the temperature is equal to or higher than 50° C. Advantageously, the reaction temperature is higher than or equal to 50° C. Preferably, it is higher than or equal to 60° C. Generally, the temperature is equal to or lower than 150° C. Advantageously, it is lower than or equal to 120° C. A most preferred range is 70° C. to 110° C.

The reaction time in a discontinuous process or the residence time in a continuous process is dependent from parameters such as reaction temperature, catalyst concentration, concentration of the starting materials and the molar ratio of the components in the reaction mixture. Generally, the reaction time or residence time can vary from 5 seconds to 20 hours.

The pressure in the reactor is usually equal to or greater than ambient pressure. It is usually lower than or equal to 15 bars (abs.), preferably lower than or equal to 10 bars.

In principle, any catalyst or catalytic system known to be active for the process according to the present invention might be used as cocatalyst. It is preferred that the reaction is performed in the absence of any other catalyst or catalytic system besides iron and phosphite.

The process according to the present invention allows for the preparation of halogenated alkanes in an efficient manner. The alkanes produced are especially suitable as intermediates in chemical synthesis. For example, they can be fluorinated. The fluorinated products are useful, for example, as solvents, refrigerants or blowing agents. A part or, preferably, all of the chlorine atoms are substituted by fluorine atoms.

A process for the preparation of hydrofluorocarbons wherein a halogenated hydrocarbon prepared according to the addition reaction according to the invention is fluorinated, is also an embodiment of the present invention. The overall process is preferably performed in a 2-step process: in the first step, the addition reaction is performed to produce the halogenoalkane, and in the second step, the fluorination reaction is performed, preferably to obtain hydrofluoroalkanes, i.e. all chlorine atoms are substituted by fluorine atoms. The fluorination can be easily accomplished by reacting the halogenoalkanes obtained by the process of the present invention with HF which advantageously is anhydrous. The chlorine-fluorine exchange can be performed with or without added fluorination catalyst. Suitable fluorination catalysts are salts of antimony, salts of titanium, salts of tantalum or salts of tin. The halide salts, especially the fluorides, chlorides or chlorofluorides are preferred salts. Other suitable fluorination catalysts are compounds of chromium, aluminium and zirconium; the oxides are preferred compounds for catalyzing fluorination reactions.

Specific examples of hydrofluorocarbons have the general formula $C_nH_{(2n+2)-p}F_p$. In this formula, n is an integer and is 3 or 4, and p is an integer and is 3, 4, 5, 6 or 7. Especially preferred hydrofluorocarbons are 1,1,1,3,3-pentafluoropropane, 1,1,1,3,3,3-hexafluoropropane and 1,1,1,3,3-pentafluorobutane.

The following examples are intended to explain the invention further without limiting it.

EXAMPLE 1

Reaction in the Presence of Tri-n-butylphosphite 2-chloroprop-1-ene, tetrachloromethane, iron and tri-n-butylphosphite, molar ratio of 2-chloroprop-1-ene and tetrachloromethane 1:2, iron and 2-chloroprop-1-ene 0.005:1, tri-n-butylphosphite and 2-chloroprop-1-ene 0.107:1 were mixed in a stainless steel autoclave. The mixture was heated to 90° C. After 5 hours, the reaction mixture was analyzed. Conversion of 2-chloroprop-1-ene was 94.3%, selectivity to 1,1,1,3,3-pentachlorobutane was 75.3%.

EXAMPLE 2

Reaction in the Presence of Triethylphosphite 2-chloroprop-1-ene, tetrachloromethane, iron and triethylphosphite, molar ratio of 2-chloroprop-1-ene and tetrachloromethane 1:2, iron and 2-chloroprop-1-ene 0.007:1, triethylphosphite and 2-chloroprop-1-ene 0.121:1 were mixed in a stainless steel autoclave and kept at 90° C. for 5 hours. Conversion of 2-chloroprop-1-ene was 70.2%, selectivity to 1,1,1,3,3-pentachlorobutane was 75.5%.

EXAMPLE 3

Fluorination to 1,1,1,3,3-pentafluorobutane 1,1,1,3,3-pentachlorobutane prepared in example 1 or example 2 can be reacted in a subsequent step with HF in the presence of a catalyst to produce 1,1,1,3,3-pentafluorobutane.

The invention claimed is:

1. A process for the preparation of halogenated hydrocarbons with at least 3 carbon atoms by the reaction of a haloalkane and an olefin which is substituted by at least one halogen atom and which is selected from isomers of chloropropene in the presence of iron and a phosphite, wherein the reaction is carried out at a temperature equal or higher than 50° C. and lower than or equal to 110° C.

2. The process according to claim 1 wherein the olefin corresponds to the formula $R^1R^2C$=$CClR^3$, wherein $R^1$, $R^2$ and $R^3$ independently represent H or Cl, linear, branched or cyclic alkyl or alkenyl, an aryl or a heteroaryl group, or substituted alkyl, alkenyl, aryl or heteroaryl groups.

3. The process according to claim 1 wherein the haloalkane has one to three carbon atoms and is substituted by at least two chlorine atoms, or wherein the haloalkane has one to three carbon atoms and is substituted by at least two chlorine atoms, and is substituted by other halogen atoms or by alkyl or halogenoalkyl groups.

4. The process according to claim 3 wherein the haloalkane is selected from the group consisting of dichloromethane, trichloromethane, tetrachloromethane, 1,1,1-trichloroethane, and 1,1,1-trichloro-3,3,3-trifluoroethane.

5. The process according to claim 1 wherein the phosphite corresponds to the formula $PR^1R^2R^3$ wherein $R^1$, $R^2$ and $R^3$ are the same or different and are alkoxy groups of the formula $R^4O$ wherein $R^4$ is a saturated C1 to C10 alkyl group, or phenoxy groups of the formula $R^5O$ wherein $R^5$ denotes phenyl.

6. The process according to claim 5 wherein $R^4$ denotes a C1 to C5 alkyl group.

7. The process according to claim 6 wherein the phosphite is selected from the group consisting of tri-ethylphosphite, tri-n-propylphosphite and tri-n-butylphosphite.

8. A process for the preparation of hydrofluorocarbons wherein a halogenated hydrocarbon prepared according to claim 1 is fluorinated.

9. The process according to claim 1 wherein the isomers of chloropropene are selected from the group consisting of 1-chloroprop-1-ene, 2-chloroprop-1-ene, and 3-chloroprop-1-ene.

10. The process according to claim 1 wherein the reaction is carried out at a temperature from 70° C. to 110° C.

* * * * *